United States Patent
Burroughs-Tencza

(12) 
(10) Patent No.: US 7,410,769 B2
(45) Date of Patent: Aug. 12, 2008

(54) PEPTIDE BIOSENSORS FOR ANTHRAX PROTEASE

(75) Inventor: Sarah Burroughs-Tencza, Pittsburgh, PA (US)

(73) Assignee: Cellomics Inc., Pittsburgh, PA (US)

( * ) Notice: Subject to any disclaimer, the term of this patent is extended or adjusted under 35 U.S.C. 154(b) by 846 days.

(21) Appl. No.: 10/182,303

(22) PCT Filed: Feb. 9, 2001

(86) PCT No.: PCT/US01/04253

§ 371 (c)(1),
(2), (4) Date: Nov. 22, 2002

(87) PCT Pub. No.: WO01/59149

PCT Pub. Date: Aug. 16, 2001

(65) Prior Publication Data

US 2003/0166028 A1    Sep. 4, 2003

Related U.S. Application Data

(60) Provisional application No. 60/182,011, filed on Feb. 11, 2000.

(51) Int. Cl.
*G01N 33/53* (2006.01)
*A61K 38/00* (2006.01)

(52) U.S. Cl. .................. 435/7.1; 435/34; 435/235.1; 530/300; 530/350

(58) Field of Classification Search .............. 435/7.1, 435/34, 235.1; 530/300, 350
See application file for complete search history.

(56) References Cited

U.S. PATENT DOCUMENTS

| | | | |
|---|---|---|---|
| 5,605,809 A | 2/1997 | Komoriya et al. | |
| 5,693,616 A | 12/1997 | Krstenansky et al. | |
| 5,981,200 A | 11/1999 | Cubitt | |
| 5,989,835 A | 11/1999 | Dunlay et al. | |
| 6,037,137 A | 3/2000 | Komoriya et al. | |
| 6,103,479 A | 8/2000 | Taylor | |
| 6,955,891 B2 * | 10/2005 | Cunningham et al. | 435/34 |

FOREIGN PATENT DOCUMENTS

| | | |
|---|---|---|
| WO | WO 94/28166 | 12/1994 |
| WO | WO 97/40065 | 10/1997 |
| WO | WO 98/37226 | 8/1998 |
| WO | WO 99/50439 | 10/1999 |
| WO | WO 00/50872 | 8/2000 |
| WO | WO 00/73437 | 12/2000 |

OTHER PUBLICATIONS

Thomas E. Creighton, in his book, Proteins: Structures and Molecular Properties, 1984, (pp. 314-316).*
Briggs et al. (European Journal of Cancer, 1993, vol. 29A, No. 2, pp. 230-237).*
Swiss-Prot online, "MEK1, MEK2, MPK6", Abstract.
G. Vitale, et al., (2000), Biochemistry Journal, "Susceptibility of mitogen-activated protein kinase kinase family members to proteolysis by anthrax lethal factor", vol. 352, pp. 739-745.
Klimpel et al., (1994) Mol Microbiol., "Anthrax toxin lethal factor contains a zinc metalloprotease consensus sequence which is required for lethal toxin activity", vol. 13, pp. 1093-1100.
Duesbery, et al., (1998) Science, "Proteolytic inactivation of MAP-Kinase-Kinase by anthrax lethal factor", vol. 280, pp. 734-737.
Vitale et al., (1998) Biochem Biophys Res Commun, "Anthrax lethal factor cleaves the N-Terminus of MAPKKs and induces tyrosine/threonin phosphorylation of MAPKs in cultured macrophages", vol. 248, pp. 706-711.
Knight, C.G. (1995) Methods Enzymol, "Fluorimetric assays of proteolytic enzymes" vol. 248, pp. 18-34.
Soleilhac et al., (1996) Anal Biochem, "A sensitive and rapid fluorescence-based assay for determination of tetanus toxin peptidase activity", vol. 241, pp. 120-127.
Hammond and Hanna (1998) Infection & Immunity, "Lethal factor active-site mutations affect catalytic activity in vitro", vol. 66, pp. 2374-2378.
Wu and Brand, (1994), Resonance energy transfer; methods and applications. Anal Biochem, "Resonance energy transfer: Methods and Applications", vol. 218 (1), pp. 1-13.
Bark et al., (2000), J. Am. Chem. Soc., "A highly efficient method for site-specific modification of unprotected peptides after chemical synthesis", vol. 122(15), p. 3573.

* cited by examiner

*Primary Examiner*—Long V. Le
*Assistant Examiner*—Lisa V Cook
(74) *Attorney, Agent, or Firm*—McDonnell Boehnen Hulbert & Berghoff LLP

(57) ABSTRACT

The present invention provides a protease biosensor that can be used to detect the presence of the lethal factor protease from *Bacillus anthracis*, as well as methods for using the protease biosensor.

3 Claims, 5 Drawing Sheets

PEPTIDE BIOSENSORS FOR ANTHRAX PROTEASE

CROSS REFERENCE

This application claims priority to U.S. Patent Application Ser. No. 60/182,011 filed Feb. 11, 2000, is a US national phase application of PCT/US01/04253, filed Aug. 16, 2001 and is related to U.S. patent application Ser. No. 09/430,656 filed Oct. 29, 1999, now U.S. Pat. No. 6,756,207.

U.S. GOVERNMENT RIGHTS

This invention was made in part with support from the U.S. Government under Contract No. N00014-98-C-0326, awarded by the U.S. Office of Naval Research, an organization of the U.S. Department of Defense. The U.S. Government may have certain nonexclusive rights in this invention.

FIELD OF THE INVENTION

This invention is in the field of fluorescence-based cell and molecular biochemical assays for toxin detection and drug discovery.

BACKGROUND OF THE INVENTION

Bacillus anthracis is the causative agent of anthrax, which is characterized by the hyperstimulation of host macrophage inflammatory pathways, leading to dramatic hypotension, shock, and death of the host. One of the toxins produced by this organism is lethal factor (LF), which is a zinc metalloprotease (Klimpel et al., (1994) *Mol Microbiol* 13, 1093-100). This protease has been found to cleave MEK1 and MEK2, members of the group of MAP-kinase-kinases (Duesbery, et al., (1998) *Science* 280, 734-737: Vitale et al., (1998) *Biochem Biophys Res Commun* 248, 706-11). It is believed that cleavage of these signaling kinases by LF leads to inhibition of growth-factor response pathways, further leading to macrophage death. It has been determined that the site of action of LF protease is within the first 12 amino acid residues of MEK1 (Vitale et al., (1998)), between the proline and isoleucine residues.

Fluorescence resonance energy transfer (FRET) can occur between a donor and acceptor fluorophores if the emission spectrum of the donor overlaps the absorption spectrum of the acceptor. The acceptor need not be fluorescent. In addition to this spectral overlap, the two fluorophores must be within a certain distance of each other and must be aligned properly. Because there is a close relationship between donor-acceptor distance and efficiency of energy transfer, measurement of this efficiency can be used to determine distance. FRET has been extensively used to measure donor-acceptor distances both within a single macromolecule and among freely diffusing molecules (of which a high concentration is required). At low concentrations in solution, FRET will only occur if the donor and acceptor are physically constrained, for example attached to the same peptide. Upon physical separation of the donor and acceptor, which might occur if the peptide were to be cleaved by a protease, the donor and acceptor would diffuse away from one another and FRET would not occur. This principle has been used to design FRET-based biosensors and assays for detecting proteolytic enzymes (Knight, C. G. (1995) *Methods Enzymol* 248, 18-34).

FRET-based biosensors can be measured in the presence of the products and reactants, and thus no separation steps are necessary, as is sometimes the case with fluorescent substrates. In addition, the FRET measurement is a ratio-based measurement, so the result is intensity independent (as long as it is within the range of detectability).

We have previously described the production of a class of fluorescent protease biosensors (U.S. patent application Ser. No. 09/430,656 filed Oct. 29, 1999, incorporated by reference herein in its entirety), as has another group (U.S. Pat. Nos. 5,605,809 and 6,037,137). A fluorescence-based tetanus toxin assay has been described (Soleilhac et al., (1996) *Anal Biochem* 241, 120-7), but it requires separation of the products from the reactants and is not FRET based. An international patent application by Duesbery et al. (WO 99/50439) lists methods for screening modulators, homologues and mimetics of LF protease activity but they either require laborious analysis methods or are extremely general. The use of peptides as substrates for LF protease activity was described by Hammond and Hanna ((1998) *Infection & Immunity* 66, 2374-8); however the peptides were not fluorescently labeled and were analyzed by high-performance liquid chromatography, which is a tedious and costly procedure.

SUMMARY OF THE INVENTION

The present invention provides FRET-based protease biosensors, and kits containing them, for detecting the presence of the anthrax protease, as well as methods for using the protease biosensors to detect the presence of *Bacillus anthracis* in a test sample. The present protease biosensors and assays provide a significant improvement over previous biosensors and assays for detecting the presence of *Bacillus anthracis* in a sample, by significantly improving both the speed and efficiency of the assay, and by detecting live, virulent strains of *Bacillus anthracis*. Therefore, the biosensors of the present invention will have fewer false positives, which is desirable for a sensor to be used in a potentially hazardous situation.

DETAILED DESCRIPTION OF THE INVENTION

Figure 1:
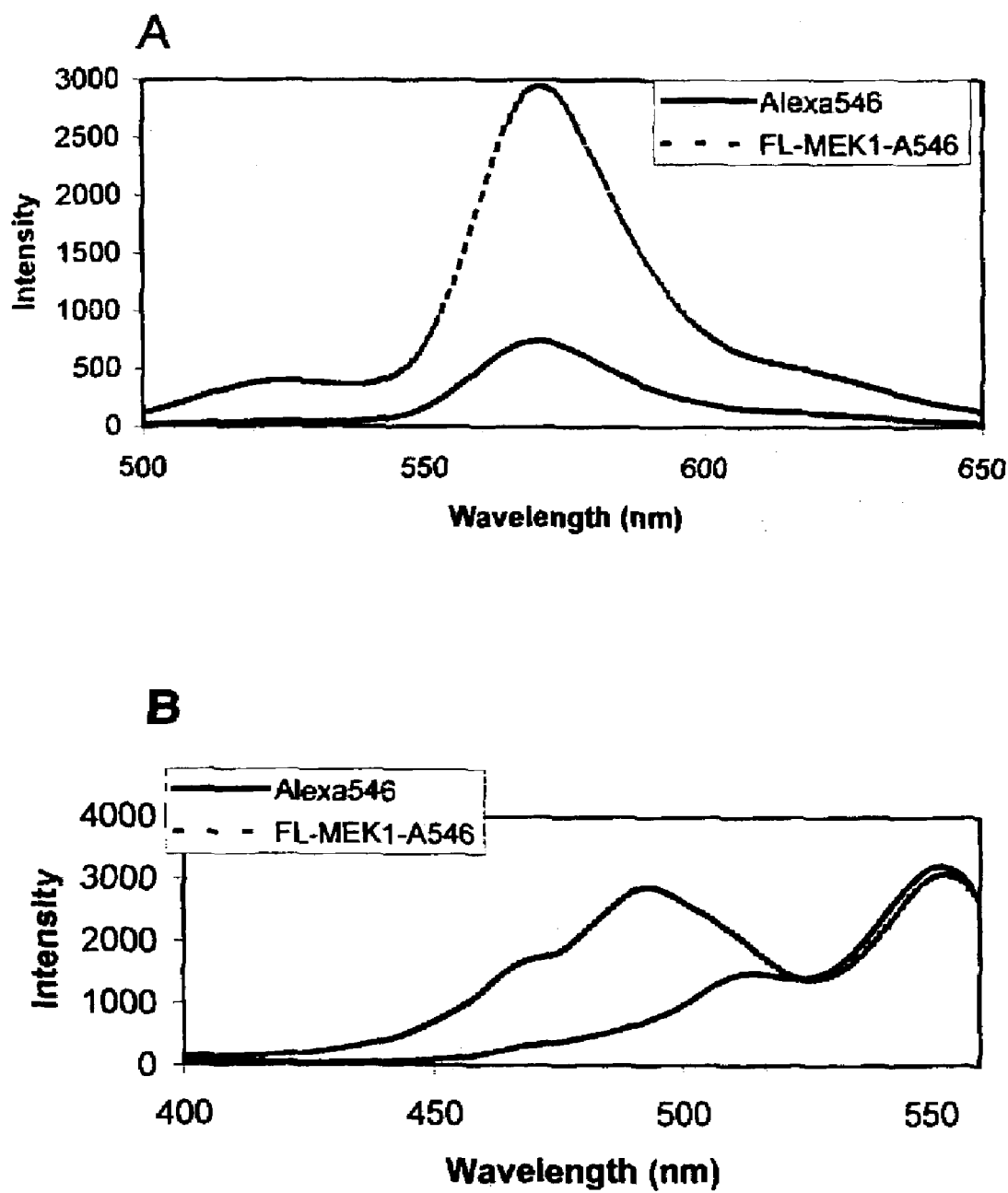
FIG. 1. Fluorescence spectra of FL-MEK1-A546 peptide and free ALEXA FLUOR® 546. Panel A, emission spectra (ex=493 nm). Panel B, excitation spectra (em=570 nm). Samples were normalized for equal absorbance (0.1) at 555 nm, the absorbance maximum of ALEXA FLUOR® 546.

In one embodiment, the present invention provides FRET-based protease biosensors that can be used to detect the presence of *Bacillus anthracis* lethal factor in a test sample. In one embodiment, the protease biosensor comprises a) a peptide comprising an amino acid sequence of the general formula I:

X-Pro-Y-Z-W wherein X is a sequence of between 5 and 13 amino acids, wherein at least one amino acid is selected from the group consisting of Arg, Lys, or His, and wherein none are Asp or Glu;

Y is selected from the group consisting of hydrophobic amino acids or Gly;

Z is selected from the group consisting of uncharged amino acids; and

W is a sequence of between 2 and 10 amino acids of any type;

wherein a cleavage site for lethal factor is between the Pro and Y residues;

b) a fluorescent donor molecule attached to the peptide that is capable of participating in fluorescence resonance energy transfer; and c) an acceptor molecule attached to the peptide that has an absorption spectrum overlapping the emission spectrum of the donor molecule, wherein the fluorescence donor molecule and the acceptor molecule are attached to amino acid residues that are on opposite sides of the cleavage site.

Fluorescence resonance energy transfer (FRET) occurs between the two fluorophores in the absence of a protease that cleaves the peptide. In the presence of the protease, cleavage of the peptide results in separation of the two fluorophores and loss of FRET. Thus the biosensor functions by reporting the activity of a protease by a change in FRET between two fluorophores separated by the protease cleavage sequence. The fluorescent donor typically is excited by incident radiation at a particular wavelength which it then re-emits at a different (longer) wavelength. When the donor fluorophore is held in close proximity to the acceptor molecule, the acceptor absorbs the light that would have been emitted by the fluorescent donor, thereby quenching the fluorescence signal of the donor molecule. Cleavage of the peptide joining the fluorescent donor and the acceptor results in separation of the two molecules, release of the quenching effect and an increase in intensity of emission spectrum of the donor molecule.

The sequence of the peptide portion of the biosensor is derived from the native MEK1 recognition site for lethal factor, KKKPTPIQLN (SEQ ID NO:1), as well as the MEK2 (RRKPVLPALTI; SEQ ID NO:14) and MEK6 (SQQRN-PGLIPK; SEQ ID NO:15) recognition sites for lethal factor.

These recognition sites for lethal factor each require the presence of the proline residue followed by a hydrophobic residue or a glycine residue, between which lethal factor cleaves. The recognition sites further require an uncharged amino acid following the hydrophobic residue, and at least one positively charged amino acid (and no negatively charged amino acid, such as Asp and Glu) within the 5 amino acids to the N-terminal side of the proline residue. Other residues in the sequence provide appropriate spacing between the critical residues or between the donor and acceptor, and thus their composition is not critical, and can include any natural or unnatural amino acid.

The range of optimal lengths for the peptide backbone of the biosensor depends on several factors including the secondary structure of the peptide (which would alter the through-space distance between the donor and acceptor), the spectral overlap between the donor and acceptor (a greater overlap generally allows longer peptide length), and the flexibility of the attachment of the peptide to the dye. For example, if a linker is used to attach the dye to the peptide and the linker is not flexible (i.e.: can not rotate about the axis of the bond(s) between the peptide and the dye), then the alignment of the dye molecule could be optimal and FRET would be very efficient, or the alignment could be very poor and there would be no FRET. If a flexible linker is used (i.e.: can rotate about the axis of the bond(s) between the peptide and the dye), an averaging effect would be caused between the best and worst case alignments, leading to an average FRET response. An explanation of how each of these factors contributes to the efficiency of FRET can be found in Knight, *Fluorimetric assays of proteolytic enzymes,* Methods Enzymol, 1995, 248: p. 18-34) and Wu and Brand, *Resonance energy transfer: methods and applications,* Anal Biochem, 1994, 218(1): p. 1-13).

In one preferred embodiment, using the donor-acceptor pairs exemplified herein, the peptide portion of the protease biosensor is between 10 and 18 amino acids in length, and more preferably is between 10 and 15 amino acids in length.

In a preferred embodiment, "Y" is selected from the group consisting of Ile, Tyr, Val, Leu, Ala, Phe, and Gly. In a further preferred embodiment, "Z" is selected from the group consisting of Ile, Tyr, Val, Leu, Ala, Phe, Gly, Gln, Asn, Ser, Thr, Trp, Pro, Met, and Ile.

In another preferred embodiment, the acceptor molecule is fluorescent, which permits detection of the fluorescence emission of both the donor and acceptor, thus providing the ability to determine a ratio of the fluorescence of the donor and acceptor molecules.

In a preferred embodiment, the peptide comprises an amino acid sequence of general formula II:

R1-R2-R3-R4-R5-Pro-R6-R7-R8-R9 wherein R1, R2, R3, R4, and R5 can be any amino acid residue with the proviso that at least one is selected from the group consisting of Arg, Lys, and His, and with the further proviso that none are Asp or Glu;

R6 comprises any hydrophobic amino acid or Gly;

R7 comprises any uncharged amino acid except Cys; and

R8 and R9 can be any amino acid;

In this embodiment it is preferred that at least two, and more preferably three, of R1, R2, R3, R4, and R5 are selected from the group consisting of Arg, Lys, and His, and even more preferred that R1, R2, and R3 are selected from the group consisting of Arg, Lys, and His.

In other preferred embodiment, R6 is selected from the group consisting of Ile, Tyr, Val, Leu, Ala, Phe, and Gly; and R7 is selected from the group consisting of Ile, Tyr, Val, Leu, Ala, Phe, Gly, Gln, Asn, Ser, Thr, Trp, Pro, Met, and Ile.

In this embodiment, it is also preferred that R9 or the C-terminal residue (when R9 is not the C-terminal residue) is selected to allow for site specific labeling of the peptide. In this embodiment, the peptide is selected from the group consisting of Cys, Lys, and N-methylaminooxy amino acid; wherein if R9 or the C-terminal residue is Lys, then none of R1, R2, R3, R4, and R5 are Lys. A recent reference discloses the use of the unnatural amino acid N-methylaminooxy amino acid for incorporation into a peptide sequence and labeling by a suitably reactive dye, including but not limited to a succinimide ester of rhodamine, fluorescein, and Cy3 (Amersham Pharmacia) (Bark et al., J. Am. Chem. Soc. 2000 122(15):3567-3573.) When R9 or the C-terminal residue is a lysine residue, an amine-reactive dye can be used to selectively label the R9 position. Such amine-reactive dyes include but are not limited to isothiocyanate or succinimide ester derivatives of commercially available dyes including but not limited to most ALEXA FLUOR® dyes (Molecular Probes, Eugene Oreg.), as well as fluorescein, rhodamine, eosin, and Cy3. Other methods for specifically incorporating dyes into peptides are well known to those skilled in the art.

Alternatively, R9 or the C-terminal residue of general formula I is Cys and is used to link a thiol-specific fluorophore, such as ALEXA-FLUOR® 546 maleimide, BODIPY® 530/550 iodoacetamide, eosin-5-maleimide, and QSY™-7 maleimide (all available from Molecular Probes, Eugene, Oreg.). In this alternative, it is preferred that R9 or the C-terminal residue of general formula I is Cys and is used to link ALEXA-FLUOR® 546 maleimide.

In another preferred embodiment, the acceptor molecule comprises fluorescein.

In another preferred embodiment, the peptide portion of the biosensor comprises a sequence of general formula III:

R1-R2-R3-R4-R5-Pro-R6-R7-R8-R9-R10-R11, wherein R1 is selected from the group consisting of Arg, Lys, Ser, and His;

R2 is selected from the group consisting of Arg, Lys, His, and Gln;

R3 is selected from the group consisting of Arg, Lys, His, Pro, and Gln;

R4 is selected from the group consisting of Pro, Val, and Arg;

R5 is selected from the group consisting of Thr, His, Arg, Leu, and Asn;

R6 is selected from the group consisting of Ile, Tyr, Val, Ala, Leu, Gly, and Phe;

R7 is selected from the group consisting of Gln, Tyr, Leu, and Pro;

R8 is selected from the group consisting of Leu, Ile, and Thr;

R9 is selected from the group consisting of Asn, Ile, and Pro;

R10 is absent or is selected from the group consisting of Pro and Lys; and

R11 is absent or is selected from the group consisting of Cys, Lys, and N-methylaminooxy amino acid; wherein if R11 is Lys, then none of R1, R2, and R3 are Lys.

In a further preferred embodiment, the peptide component of the protease biosensor comprises an amino acid sequence selected from the group consisting of:

a) Met-Pro-Lys-Lys-Lys-Pro-Thr-Pro-Ile-Gin-Leu-Asn-Pro (SEQ ID NO:2);

b) Met-Pro-Lys-Lys-Lys-Pro-Thr-Pro-Ile-Gln-Leu-Asn-Pro-Cys (SEQ ID NO:3);

c) Met-Pro-Lys-Lys-Lys-Pro-Thr-Pro-Ile-Tyr-Leu-Asn-Pro-Cys (SEQ ID NO:4);

d) Met-Pro-Lys-Lys-Lys-Pro-His-Pro-Ile-Gln-Leu-Asn-Pro-Cys (SEQ ID NO:5);

e) Met-Pro-Lys-Lys-Lys-Pro-His-Pro-Ile-Tyr-Leu-Asn-Pro-Cys (SEQ ID NO:6);

f) Met-Pro-Lys-Lys-Lys-Pro-Thr-Pro-Tyr-Gln-Leu-Asn-Pro-Cys (SEQ ID NO:7);

g) Met-Pro-Lys-Lys-Lys-Pro-Thr-Pro-Ile-Pro-Leu-Asn-Pro-Cys (SEQ ID NO:8);

h) Met-Pro-His-His-His-Pro-Thr-Pro-Ile-Gln-Leu-Asn-Pro-Cys (SEQ ID NO:9);

i) Met-Pro-His-His-His-Pro-Thr-Pro-Ile-Tyr-Leu-Asn-Pro-Cys (SEQ ID NO: 10);

j) Met-Pro-Lys-Lys-Lys-Pro-Thr-Pro-Val-Gln-Leu-Asn-Pro-Cys (SEQ ID NO:11);

k) Met-Pro-Lys-Lys-Lys-Pro-Thr-Pro-Phe-Gln-Leu-Asn-Pro-Cys (SEQ ID NO: 12);

l) Met-Pro-Lys-Lys-Lys-Pro-Arg-Pro-Ile-Gln-Leu-Asn-Pro-Cys (SEQ ID NO:13);

m) Arg-Arg-Lys-Pro-Val-Leu-Pro-Ala-Leu-Thr-Ile (SEQ ID NO: 14); and n) Ser-Gln-Gln-Arg-Asn-Pro-Gly-Leu-Ile-Pro-Lys (SEQ ID NO:15)

In a further preferred embodiment, the peptide component of the protease biosensor comprises an amino acid sequence selected from the group consisting of:

a) Met-Pro-Lys-Lys-Lys-Pro-Thr-Pro-Ile-Gln-Leu-Asn-Pro (SEQ ID NO:2);

b) Met-Pro-Lys-Lys-Lys-Pro-Thr-Pro-Ile-Gln-Leu-Asn-Pro-Cys (SEQ ID NO:3);

c) Met-Pro-His-His-His-Pro-Thr-Pro-Ile-Gln-Leu-Asn-Pro-Cys (SEQ ID NO:9);

d) Met-Pro-His-His-His-Pro-Thr-Pro-Ile-Tyr-Leu-Asn-Pro-Cys (SEQ ID NO: 10);

e) Arg-Arg-Lys-Pro-Val-Leu-Pro-Ala-Leu-Thr-Ile (SEQ ID NO: 14); and f) Ser-Gln-Gln-Arg-Asn-Pro-Gly-Leu-Ile-Pro-Lys (SEQ ID NO:15).

In a further preferred embodiment, the peptide component of the protease biosensor consists essentially of an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, and SEQ ID NO:15.

In another preferred embodiment, the peptide component of the protease biosensor consists essentially of an amino acid sequence of the one of the cited general formulas.

The peptides of the instant invention may be synthesized by any conventional method, including, but not limited to, those set forth in J. M. Stewart and J. D. Young, *Solid Phase Peptide Synthesis*, 2nd ed., Pierce Chemical Co., Rockford, Ill. (1984) and J. Meienhofer, *Hormonal Proteins and Peptides*, Vol. 2, Academic Press, New York, (1973) for solid phase synthesis and E. Schroder and K. Lubke, *The Peptides*, Vol. 1, Academic Press, New York. (1965) for solution synthesis. The disclosures of the foregoing treatises are incorporated by reference herein.

In general, these methods involve the sequential addition of protected amino acids to a growing peptide chain (U.S. Pat. No. 5,693,616, herein incorporated by reference in its entirety). Normally, either the amino or carboxyl group of the first amino acid and any reactive side chain group are protected. This protected amino acid is then either attached to an inert solid support, or utilized in solution, and the next amino acid in the sequence, also suitably protected, is added under conditions amenable to formation of the amide linkage. The fluorophores can be added during the solid-phase synthesis reaction, or as a later step in aqueous phase, as is known to those of skill in the art. After all the desired amino acids have been linked in the proper sequence, protecting groups and any solid support are removed to afford the crude polypeptide. The polypeptide is desalted and purified, preferably chromatographically, to yield the final product.

Preferably, peptides are synthesized according to standard solid-phase methodologies, such as may be performed on an Applied Biosystems Model 430A peptide synthesizer (Applied Biosystems, Foster City, Calif.), according to manufacturer's instructions. Other methods of synthesizing peptides or peptidomimetics, either by solid phase methodologies or in liquid phase, are well known to those skilled in the art.

Alternatively, the peptide portion of the protease biosensor can be produced via standard recombinant DNA technology. A DNA sequence encoding the desired amino acid sequence is cloned into an appropriate expression vector and used to transform a host cell so that the cell expresses the encoded peptide sequence. Methods of cloning, expression, and purification of recombinant peptides are well known to those of skill in the art. See, for example, Sambrook, et al., Molecular Cloning: A Laboratory Manual (2nd Ed., Vols. 1-3, Cold Spring Harbor Laboratory (1989)), Methods in Enzymology, Vol. 152: Guide to Molecular Cloning Techniques (Berger and Kimmel (eds.), San Diego: Academic Press, Inc. (1987)), or Current Protocols in Molecular Biology, (Ausubel, et al. (eds.), Greene Publishing and Wiley-Interscience, New York (1987). In this case, it is preferred to incorporate two unique amino acids to permit attachment of the two fluorophores, one on each end of the peptide, by the liquid phase methods.

Thus, in another aspect, the present invention provides isolated polynucleotide sequences that encode the peptide portion of the biosensors disclosed herein. In preferred embodiments, the polypeptide sequence is selected from the group consisting of:

```
ATGCCNAA(A/G)AA(A/G)AA(A/G)CCNACNCCNAT(TCA)CA(A/G)(T/C)TNAA       (SEQ ID NO:16)
(T/C)CCN, which encodes SEQ ID NO:2;

ATGCCNAA(A/G)AA(A/G)AA(A/G)CCNACNCCNAT(TCA)CA(A/G)(T/C)TNAA       (SEQ ID NO:17)
(T/C)CCNTG(T/C), which encodes SEQ ID NO:3;

ATGCCNAA(A/G)AA(A/G)AA(A/G)CCNACNCCNAT(TCA)TA(T/C)(T/C)TNAA       (SEQ ID NO:18)
(T/C)CCNTG(T/C), which encodes SEQ ID NO:4;

ATGCCNAA(A/G)AA(A/G)AA(A/G)CCNCA(T/C)CCNAT(TCA)CA(A/G)(T/C)T      (SEQ ID NO:19)
NAA(T/C)CCNTG(T/C), which encodes SEQ ID NO:5;

ATGCCNAA(A/G)AA(A/G)AA(A/G)CCNCA(T/C)CCNAT(TCA)TA(T/C)(T/C)TN     (SEQ ID NO:20)
AA(T/C)CCNTG(T/C), which encodes SEQ ID NO:6;

ATGCCNAA(A/G)AA(A/G)AA(A/G)CCNACNCCNTA(T/C)CA(A/G)(T/C)TNAA       (SEQ ID NO:21)
(T/C)CCNTG(T/C), which encodes SEQ ID NO:7;

ATGCCNAA(A/G)AA(A/G)AA(A/G)CCNACNCCNAT(TCA)CCN(T/C)TNAA(T/C)      (SEQ ID NO:22)
CCNTG(T/C), which encodes SEQ ID NO:8;

ATGCCNCA(T/C)CA(T/C)CA(T/C)CCNACNCCNAT(TCA)CA(A/G)(T/C)TNAA       (SEQ ID NO:23)
(T/C)CCNTG(T/C), which encodes SEQ ID NO:9;

ATGCCNCA(T/C)CA(T/C)CA(T/C)CCNACNCCNAT(TCA)TA(T/C)(T/C)TNAA       (SEQ ID NO:24)
(T/C)CCNTG(T/C), which encodes SEQ ID NO:10;

ATGCCNAA(A/G)AA(A/G)AA(A/G)CCNACNCCNGTNCA(A/G)(T/C)TNAA(T/C)      (SEQ ID NO:25)
CCNTG(T/C), which encodes SEQ ID NO:11;

ATGCCNAA(A/G)AA(A/G)AA(A/G)CCNACNCCNTT(T/C)CA(A/G)(T/C)TNAA       (SEQ ID NO:26)
(T/C)CCNTG(T/G)=, which encodes SEQ ID NO:12;

ATGCCNAA(A/G)AA(A/G)AA(A/G)CCN(A/C)GNCCNAT(TCA)CA(A/G)(T/C)T      (SEQ ID NO:27)
NAA(T/C)CCNTG(T/C), which encodes SEQ ID NO:13;

(A/C)GN(A/C)GNAA(A/G)CCNGTN(T/C)TNCCNGCN(T/C)TNACNAT(T/C/A),      (SEQ ID NO:28)
which encodes SEQ ID NO:14; and (A/T)(G/C)NCA(A/G)CA(A/G)(C/A)GNAA(T/C)CCNGGN(T/C)TNAT(T/C/A)CC   (SEQ ID NO:29)
NAA(A/G), which encodes SEQ ID NO:15.
```

In this embodiment, when the codon (T/C)TN is specified, it encodes leucine; when the codon (A/T)(G/C)N is specified, it encodes serine, and when the codon (A/C)GN is specified, it encodes arginine.

In this embodiment, the polynucleotide sequence is preferably double stranded and cloned into an expression vector for recombinant expression and purification of the peptide, followed by attachment of the fluorophore as described above. The polynucleotide sequence preferably encodes one or more additional amino-terminal amino acids for attaching a fluorophore. The polynucleotide may also encode one or more additional carboxy-terminal amino acids for attaching a fluorophore. In another embodiment, cells are provided that have been transfected with the expression vectors and that express the peptide portion of the biosensor.

After synthesis of the peptide component of the protease biosensor, the donor and acceptor fluorophores are attached to the peptide by any of a number of means well known to those of skill in the art. In one embodiment, the fluorophores are linked directly from a reactive site on the fluorophore to a reactive group on the peptide such as a terminal amino or carboxyl group, or to a reactive group on an amino acid side chain such as a sulfhydryl, an amino, or a carboxyl moiety. Many fluorophores normally contain suitable reactive sites. Alternatively, the fluorophores may be derivatized to provide reactive sites for linkage to the peptide portion of the biosensor. Suitable linkers are well known to those of skill in the art and include, but are not limited to, isothiocyanate, succinimide ester, maleimide, iodoacetamide, straight or branched-chain carbon linkers, heterocyclic carbon linkers, or peptide linkers. Such linkers can be used to simply increase spacing between the fluorophore(s) and the peptide, or to provide sites for functional interaction between the fluorophore(s) and the peptide. Fluorophores derivatized with functional groups for linking to a second molecule are commercially available from a variety of manufacturers. The derivatization may be by a simple substitution of a group on the fluorophore itself, or may be by conjugation to a linker.

The fluorophores need not be attached to the end of the peptide. For example, the fluorophores can be attached to the amino terminus of the peptide via a direct peptide bond, alternatively, the fluorophores may be linked to maleimide or iodoacetamide for attaching the fluorophore to a cysteine residue, or may be linked to isothiocyanate or succinimide ester for attaching the fluorophore to a lysine or the amino terminus of the peptide biosensor. The amino acid to which the fluorophore is attached is preferably unique within the peptide and can be placed anywhere within the peptide sequence, so long as the two fluorophores are across the cleavage site from each other and their presence does not interfere with protease activity.

The "donor" and "acceptor" fluorophores are typically selected as a matched pair wherein the absorption spectra of the acceptor molecule significantly overlaps the emission spectrum of the donor molecule. Preferably, the fluorescent donor and acceptor are selected such that both the absorption and the emission spectrum of the donor molecule is in the visible range (400 nm to about 700 nm), facilitating the detection of protease activity in solution, cells, biological fluids, tissue homogenates, tissue sections, and other relevant sources. The emission spectra, absorption spectra and chemical composition of many fluorophores are well known to those of skill in the art (see, for example, Handbook of Fluorescent Probes and Research Chemicals, R. P. Haugland, ed. which is incorporated herein by reference). The overlaps of many donor-acceptor pairs are listed in Wu and Brand [2]. (Wu, P. and L. Brand, *Resonance energy transfer: methods and applications.* Anal Biochem, 1994, 218(1): p. 1-13) Preferred fluorophore pairs include, but are not limited to fluorescein or ALEXA FLUOR® 488 (donor)+rhodamine, eosin, erythrosin, QSY-7, ALEXA FLUOR® 546, BODIPY®-TMR Cy3, or ALEXA FLUOR® 532(acceptor); ALEXA FLUOR® 532 (donor)+ALEXA® 546 or rhodamine (acceptor); ALEXA FLUOR®350 (donor)+ALEXA FLUOR® 430 (acceptor); ALEXA FLUOR®430 (donor)+ALEXA FLUOR® 532, eosin, rhodamine, or Cy3 (acceptor). (Cy3 is available from Amersham Pharmacia; all others available from Molecular Probes, Eugene, Oreg.)

Choice of an acceptor molecule depends on the above as well as availability of suitably reactive derivatives of the acceptor and its solubility (more soluble fluorophores are preferred). For example, labeling of the FRET-based peptide biosensors of the present invention with both fluorescein and eosin resulted in a non-soluble product. For the purposes of measuring protease activity in solution, the sensor itself must be soluble in aqueous (preferably saline) solution.

The position of the donor and acceptor fluorophores on the peptide may vary, but they must be on opposite sides of the peptide cleavage site and must not interfere with protease activity. It is possible that the particular attachment of each dye may result in poor alignment with respect to each other, resulting in low efficiency of energy transfer in spite of good overlap. However the use of soluble fluorophores with freely-rotating linkers (as discussed above) between the peptide and the dye make this possibility very unlikely. The linkers may be joined to the carboxyl and amino terminal amino acids through their side groups (e.g., through a disulfide linkage to cysteine). In a preferred embodiment, the donor and acceptor fluorophores are attached to opposite ends of the peptide portion of the biosensor.

In a further preferred embodiment, R9 in general formula II or R11 in general formula III is Cys and is used to link a thiol-specific fluorophore, such as ALEXA-FLUOR® 546 maleimide, BODIPY® 530/550 iodoacetamide, eosin-5-maleimide, and QSY™-7 maleimide (all available from Molecular Probes, Eugene, Oreg.), in a most preferred embodiment. R9 in general formula II or R11 in general formula III is Cys and is used to link ALEXA-FLUOR® 546 maleimide In another preferred embodiment, the acceptor molecule comprises fluorescein.

The protease biosensors of the present invention may be obtained in solution or linked to a solid support. Such a "solid support" can comprise any solid material that does not dissolve in or react with any of the components present in the solutions utilized for assaying for protease activity, and that provides a functional group for attachment of the biosensor. Solid support materials are well known to those of skill in the art and include, but are not limited to silica, controlled pore glass (CPG), polystyrene, polystyrene/latex, carboxyl modified TEFLON™, dextran, derivatized polysaccharides such as agar bearing amino, carboxyl or sulfhydryl groups, and various plastics such as polyethylene and acrylic. The solid supports may be derivatized with functional groups (e.g. hydroxyls, amines, carboxyls, esters, and sulfhydryls) to provide reactive sites for the attachment of linkers or the direct attachment of the peptide. The protease biosensor may be linked to the solid support directly through the peptide backbone, or through the fluorophore either directly or via a linker.

In another aspect of the present invention, a solution-phase method for detecting the presence of lethal factor from *Bacillus anthracis* in a test sample, is provided, comprising
a) providing one or more protease biosensors as disclosed above;
b) contacting the protease biosensor(s) with the test sample; and
c) measuring fluorescence resonance energy transfer from the protease biosensor, wherein an increase in the emission spectra of the donor molecule indicates the presence of lethal factor from *Bacillus anthracis* in the test sample. In a preferred embodiment in which both the donor and the acceptor are fluorescent, fluorescence resonance energy transfer is detected by measuring the ratio of emission from the donor and the acceptor, where the ratio of donor:acceptor emission intensity increases in the presence of the lethal factor.

In another aspect of the present invention, a cell-based method for detecting the presence of lethal factor from *Bacillus anthracis* in a test sample, is provided, comprising a) providing one or more protease biosensors as disclosed above;

b) loading the protease biosensor(s) into cells to be analyzed;

c) contacting the cells with the test sample;

d) measuring cell-based fluorescence resonance energy transfer from the protease biosensor, wherein an increase in the emission intensity of the donor indicates the presence of lethal factor from *Bacillus anthracis* in the test sample.

In a preferred embodiment of these methods, the contacting of the protease biosensor or the cells is carried out in the presence of generalized protease inhibitors that do not interfere with lethal factor activity, including but not limited to AEBSF (4-(2-aminoethyl)benzenesulfonylfluoride), aprotinin, bestatin, E-64, leupeptin, and pepstatin A.

In one embodiment, the test sample comprises an environmental sample, including but not limited to water, soil, and air samples. Alternatively, the test sample may comprise any type of cell culture fluid.

Fluorescence resonance energy transfer (FRET) occurs between the two dyes in the absence of the protease of interest. In the presence of the protease, cleavage of the peptide results in separation of the two fluorophores and loss of FRET. Thus the biosensor functions by reporting the activity of a protease by a change in FRET between two dyes separated by the protease cleavage sequence. Thus, in addition to its utility in solution-phase studies in vitro, the peptide biosensor may be loaded into cells and function as an intracellular indicator of protease activity. Such loading can be accomplished by techniques including, but not limited to, triton-mediated loading, scrape loading, syringe-loading, and microinjection. For this application the use of a fluorescent acceptor dye is preferable because it provides a signal regardless of whether it is intact or cleaved, and it enables ratio imaging. The methods can further be used to identify the presence of *Bacillus anthracis* lethal factor in any biological tissue or fluid, including but not limited to sputum, blood, serum, plasma, blood cells, tissue or fine needle biopsy samples, urine, peritoneal fluid, and pleural fluid, or cells therefrom. Biological samples may also include sections of tissues such as frozen sections taken for histological purposes The measurements can be made in a high-throughput mode in solution or in a cell without subcellular resolution by any method known in the art, including but not limited to fluorescence spectroscopy, flow cytometry, fluorescence microscopy, and by use of real-time PCR monitors (Fisher Scientific; Roche). For example, the cell screening system described in U.S. Pat. Nos. 5,989,835 and 6,103.479 could be used, both references incorporated by reference herein in their entirety. Alternatively, the measurements can be made in a high content mode with subcellular resolution by any method known in the art, such as described in U.S. Pat. Nos. 5,989,835 and 6,103,479. Additionally, the real-time reporting of the proteolytic events make this type of biosensor amenable to kinetic assays. In either case, the method can be used to detect lethal factor from a test sample, or to serve as the basis for a drug screening program to identify candidate compounds that interfere with the effect of lethal factor on a cell. In this embodiment, the cells are contacted with candidate compounds in the presence of lethal factor, and those candidate compounds that interfere with lethal factor activity can be readily identified.

The protease biosensors of the present invention can be used as part of a combined high throughput (HT)-high content (HC) cell-based screen. The protease biosensor would serve as an HT component, allowing the user to screen cells in a high-throughput mode for the presence or absence of fluorescence emission (in the green channel in the examples below). One could then examine the cells further to look at subcellular localization of various proteins in the target pathway (MEKI and ERK via immunofluorescence, for example) to determine whether the protease activity has resulted in activation or inhibition of the target pathway. In this case it would be preferable to use a non-fluorescent acceptor dye (erythrosin or QSY-7 in this example) so that the HT screen would only occupy one channel of fluorescence (green) and would go from dark to light to signal a hit. This would allow the HT measurement to run quickly and leave a separate channel (such as the red channel based on the dyes suggested here) for the HC assay.

The present invention also provides for kits for the detection of *Bacillus anthracis* lethal factor in a test sample. The kits comprise one or more of the anthrax protease biosensors disclosed above. The biosensors may be provided in solution or bound to a solid support. The kits may further comprise instructions for conducting assays using the biosensors. In addition, the kits may also include isolated polynucleotides encoding the peptide portion of the biosensor, cells expressing the peptide portion of the biosensors, other reagents, buffers, protease inhibitors, and stock proteases to aid the detection of protease activity utilizing the protease biosensors of the present invention.

EXAMPLES

Design, Synthesis, and Purification of FL-MEK1-A546. Knowing that anthrax protease cleaves MEK1 between proline and isoleucine residue within the first 12 amino acids of the protein, a 13 amino acid sequence was chosen to provide some flanking residues but keeping the length of the peptide short enough to maintain high efficiency FRET. The general strategy for synthesizing the dual-labeled peptide was similar to that described by Contillo et al. (in *Techniques in Protein Chemistry*, J. W. Crabb, Editor. 1994, Academic Press: San Diego, p. 493-500)] except that the more soluble ALEXA FLUOR® 546 fluorophore was chosen instead of the eosin, which allows for aqueous-phase reaction and purification.

A cysteine residue was added at the C-terminus to provide a site for thiol-specific labeling with the second fluorophore. The sequence of the peptide is MPKKKPTPIQLNPC (SEQ ID NO:3). The peptide was synthesized by a custom synthesis facility (BioPeptide, San Diego, Calif.) with carboxyfluorescein specifically attached to the N-terminus during solid phase synthesis. The peptide was resuspended at a concentration of approx. 10 mg/ml by weight in 0.1% acetic acid. The absorbance spectrum of the peptide, diluted 1:2000 in 100 mM Tris, pH 8.5, was recorded and used to calculate the actual concentration of the peptide based on fluorescein absorbance.

Addition of the acceptor fluorophore was accomplished by reaction of 50 nmol FL-MEKI with 500 mmol ALEXA FLUOR®R 546-maleimide (Molecular Probes) in a reaction volume of 500 μL PBS (pH 7.2). The reaction mixture was stirred overnight at 4° C. in the dark. The sample was applied to a 0.5×50 cm SEPHADEX™ GI5 chromatography column equilibrated with PBS pH 7.2, and eluted with PBS at a flow rate of 2 ml/minute, which provided a complete separation between the dye-labeled peptides and free dye.

Spectroscopic characterization. Absorbance spectra were recorded on a Hewlett-Packard 8453 UV-Visible Spectrophotometer. The molar extinction coefficients (provided by Molecular Probes) for each dye were used with the absorption spectrum of the dual-labeled peptide to calculate the molar ratio of the two dyes on the peptide. Solutions of free dye and dual-labeled peptide were prepared such that their absorbances matched, and these samples were used for fluorescence spectra acquisition.

Fluorescence Spectra. Solutions of dye or peptide with a maximal absorbance of approximately 0.1 were generally used to collect fluorescence data. Spectra were recorded in a K2 Multifrequency Phase Fluorometer (ISS, Champaign, Ill.). Temperature control for kinetics experiments was provided by a circulating water bath providing heat to the cuvette chamber. The cuvette chamber was also equipped with a stirring mechanism. Excitation and emission spectra were recorded for characterization of the dual-labeled peptide and trypsin-treated peptide. For some kinetics experiments involving proteases, the fluorometer was set up to record the emission at two fixed wavelengths at a set interval over a two-hour period. In other cases, a CYTOFLUOR® plate reader (Perseptive Biosystems, Inc.) was used to measure fluorescence intensity at two different emission wavelengths.

Cell loading. Several methods were used to try to load the fluorescent peptide into cells, including use of liposomes, TRITON™ X-100, or no additive and incubation of the peptide with adherent cells. For Triton-based loading, the following procedure was used. On the day before they were to be loaded, BHK cells were seeded into 6-well dishes at $1\times10^5$ per well. The cells were approx. 30% confluent the next day. The cells were treated with a solution of 0.001% TRITON™ X-100 in Hank's Balanced Salt Solution for 4 minutes. The saline was replaced with complete medium containing various concentrations of dual-labeled peptide, with or without additional TRITON™ X-100. The cells were incubated for 1.5 hours, then the peptide solutions were removed and complete medium was added to the wells. Cells were observed under a fluorescence microscope both immediately after peptide removal and after a 3.5 hour recovery period in the incubator. Images were acquired using an Axiovert 25 microscope and QED Imaging software. Images were saved as TIFF files and imported into Adobe Photoshop.

Results

Purification and absorbance characterization. The products of the dye-peptide reaction were separated by size-exclusion chromatography, as discussed above. The identity of the early-eluting sample was confirmed as dual-labeled peptide by its absorbance spectrum which showed the contributions of both the fluorescein (495 nm) and the ALEXA FLUOR® 546 (555 nm) to the spectrum. Subsequent reactions used increased volume and amount of reactants while maintaining the dye:peptide ratio, concentration, and reaction time. Overnight reaction (compared to 2 hours at room temperature) yielded a peptide with better quenching of the fluorescein and signal change with protease treatment, presumably due to less free fluor-peptide in the product.

Fluorescence Characterization. The dual-labeled peptide was characterized with respect to its fluorescence spectra and occurrence of FRET between the fluorescein and ALEXA FLUOR® 546. FIG. 1 shows the fluorescence excitation and emission spectra of FL-MEK1 peptide and ALEXA FLUOR® 546 maleimide, where the samples have equal absorbance at 555 nm. It is clearly seen from the FL-MEK1-A546 peptide emission spectrum (upon excitation at 493 nm; FIG. 1A) that FRET occurred between the fluorescein (donor) and the ALEXA FLUOR® 546 (acceptor), resulting in a small donor emission band and a large acceptor emission band. A spectrum of free ALEXA FLUOR® 546 at a concentration equal to that of the dye in the peptide solution is shown for comparison. If no FRET were occurring in the peptide, its spectrum (upon excitation at 493 nm) would look like that of the free dye. The excitation spectrum (emission at 570 nm; FIG. 1B) indicates that the dual-labeled peptide was excited by both 493 nm and 550 nm light, corresponding to the fluorescein and ALEXA FLUOR®, respectively. Excitation of the fluorescein in the peptide produced emission from the ALEXA FLUOR® 546 at 570 nm, indicating that FRET occurred between the two fluorophores.

Figure 2:
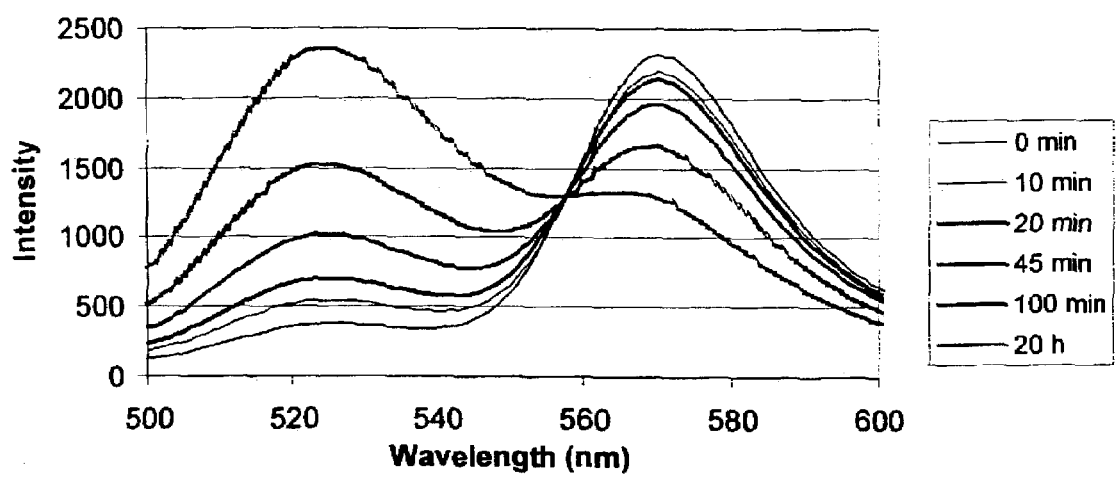
FIG. 2. Treatment of FL-MEK1-A546 with trypsin. Fluorescence emission spectra were recorded at the indicated times of incubation of the peptide with the protease. The degree of cleavage is proportional to the ratio of the intensity of the 520 nm peak to the 570 nm peak.

Protease Susceptibility of FL-MEK1-A546. In order for the dual-labeled peptide to be a biosensor of protease activity, FRET must occur only in the intact molecule and not in a proteolyzed peptide. For initial experiments, a model protease was used in place of anthrax protease, due to its limited availability. The peptide sequence used in the present study contains three lysine residues, making it a likely substrate of trypsin. Trypsin was added at a 1:10 enzyme:peptide ratio to a solution of FL-MEK1-A546 and emission spectra were recorded over time at room temperature. FIG. 2 illustrates that upon exposure to trypsin and excitation at 493 nm, the emission band of fluorescein gradually increased over time while the emission from ALEXA FLUOR® 546 decreased. These data strongly suggest that the peptide is being cleaved by trypsin and that FRET only occurs in the non-cleaved peptide, and demonstrate that the dual-labeled peptide is an indicator of trypsin activity.

Figure 3:
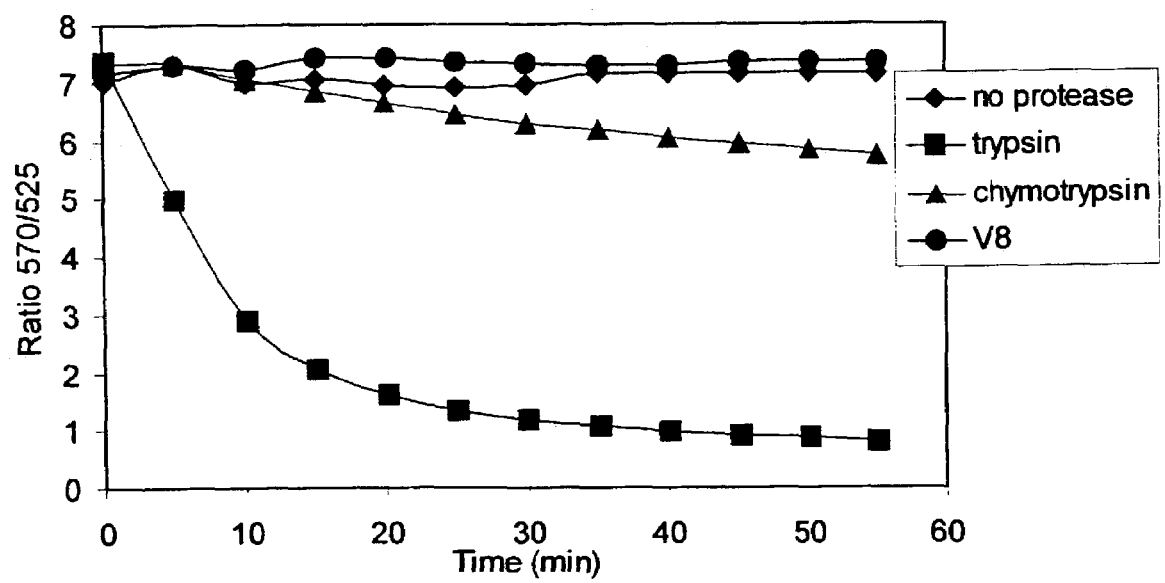
FIG. 3. Specificity/kinetics of cleavage of the peptide by proteases. Samples of peptide were treated individually with trypsin, V8, chymotrypsin, or no protease and the ratio of emission (570/525) was monitored over time. The decrease in ratio indicates a loss of FRET and cleavage by the protease.

Kinetics and Specificity of Trypsin Cleavage. A series of experiments was performed in order to address the specificity and speed of the cleavage reaction. A series of time courses were run at 37° C. in the fluorometer. Samples included FL-MEK1-A546 peptide incubated with trypsin, chymotrypsin, V8, or no protease. The emission intensities at 525 and 570 nm were measured every 5 minutes for one hour. The ratio of the 570 to 525 emission was plotted versus time in FIG. 3 to illustrate the speed and specificity of the cleavage reaction. Whereas trypsin caused a rapid reduction in the 570/525 ratio (corresponding to loss of FRET), no such decrease was observed in the no-protease or V8 protease controls. V8 protease cleaves peptides after Glu or Asp residues, so no cleavage was expected. Chymotrypsin cleaved the peptide at a rather slow rate, which was also expected because this enzyme is known to cut after Met and Leu residues with low efficiency (Tyr and Trp are the preferred targets).

The above data demonstrate the creation of a dual-labeled fluorescent peptide that detects protease activity by a change in FRET. The peptide is soluble, highly fluorescent, and appears to exhibit a high degree of FRET.

Loading of the peptide into cells. In order to use this protease substrate in a high content screen, and because the anthrax protease acts intracellularly, it is desirable to have the peptide located within cells. A method involving TRITON™ X-100 was found to be useful for this purpose. Cells were incubated in 0.001% TRITON™ in HBSS for 4 minutes, then the saline was replaced with peptide-containing complete medium and incubated for 1.5 hours. Upon replacement of the peptide-containing medium with normal complete medium, the cells were observed under the fluorescence microscope using a rhodamine filter set. Lysosomal staining of the cells was observed immediately after the peptide incubation. However, 3.5 hours after removal of extracellular peptide, the staining was more evenly distributed throughout the cell and was excluded from the nucleus. Therefore, it appears that the peptide is cytoplasmic and therefore should be accessible to an intracellular protease such as anthrax lethal toxin. Images acquired using the fluorescein filter set showed no fluorescence, indicating that the biosensor was still intact (not cleaved by an endogenous intracellular protease) at 3.5 hours post loading.

The peptide was not taken up by cells by simply placing it in the extracellular medium, indicating that the chemical properties of the peptide do not allow for transfer through the plasma membrane. Although there has been evidence that proteins can be loaded into cells using cationic liposomes, this method did not work for loading peptide; this may be due to the small size of the peptide which is not conducive to forming peptide-liposome aggregates, as well as the isoelectric point of the peptide (8.5) which would make it neutral at the pH of the aggregation step (anionic proteins are preferred).

Susceptibility of Sensor to anthrax LF protease. Aliquots of the sensor solution (2 uM in PBS, pH 7.4) were contacted with 0.1 μM trypsin, 0.1 μM chymotrypsin, 1 mM BSA, 0.2 μM anthrax LF (provided by Dr. Stephen Leppla, National Institutes of Health), or 0.1 μM anthrax LF for a period of 30 minutes at 37° C. EDTA was added to each solution to stop the reaction and inactivate LF. The fluorescence emission spectrum of each sample was recorded in a fluorometer. The ratio of emission at 570 nm to 525 nm was used as a measure of cleavage of the peptide by each protease. LF AT 0.1 μM partially digested the peptide within the 30 minute reaction time. The 0.2 μM LF and the 0.1 μM trypsin digested the peptide nearly completely (ratio <1). These data indicate that the peptide is a substrate of LF.

| Protease/Control | Ratio 570/525 |
| --- | --- |
| LF .2 uM | 0.95 |
| LF .1 uM | 1.49 |
| trypsin .1 uM | 0.63 |
| BSA | 2.30 |

Figure 4A:
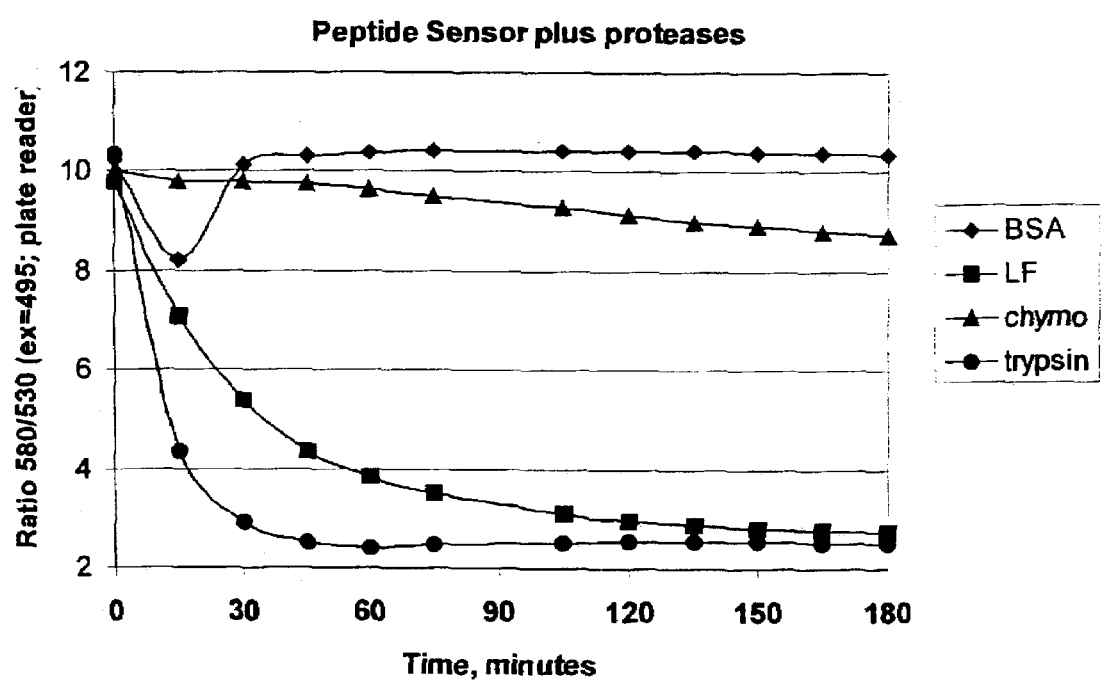
FIG. 4A shows that both trypsin and LF efficiently cleaved the substrate, with trypsin cleavage occurring at a slightly higher rate.

Kinetics of peptide cleavage by LF. Aliquots of sensor solution (2 uM in PBS, pH 6.75) were placed into the wells of a 96-well plate. To each well was added a different protease at a 1:10 protease:peptide ratio. The plate was sealed and incubated at 37° C. The fluorescence was recorded on a fluorescence plate reader (excitation:495; em1:530; em2:580). Intensity measurements were recorded at 15-minute intervals for a total of 3 hours. The emission ratio was plotted as a function of time. FIG. 4A shows that both trypsin and LF efficiently cleaved the substrate, with trypsin cleavage occurring at a slightly higher rate. This was expected due to the occurrence of three potential trypsin cleavage sites in this peptide. However, an observable difference in ratio occurred for the anthrax LF as well as the trypsin. Chymotrypsin cleaved the peptide at a much lower rate, whereas incubation at 37° C. with no protease (BSA control) indicated no non-specific hydrolysis of the peptide occurred during this period.

Figure 4B:
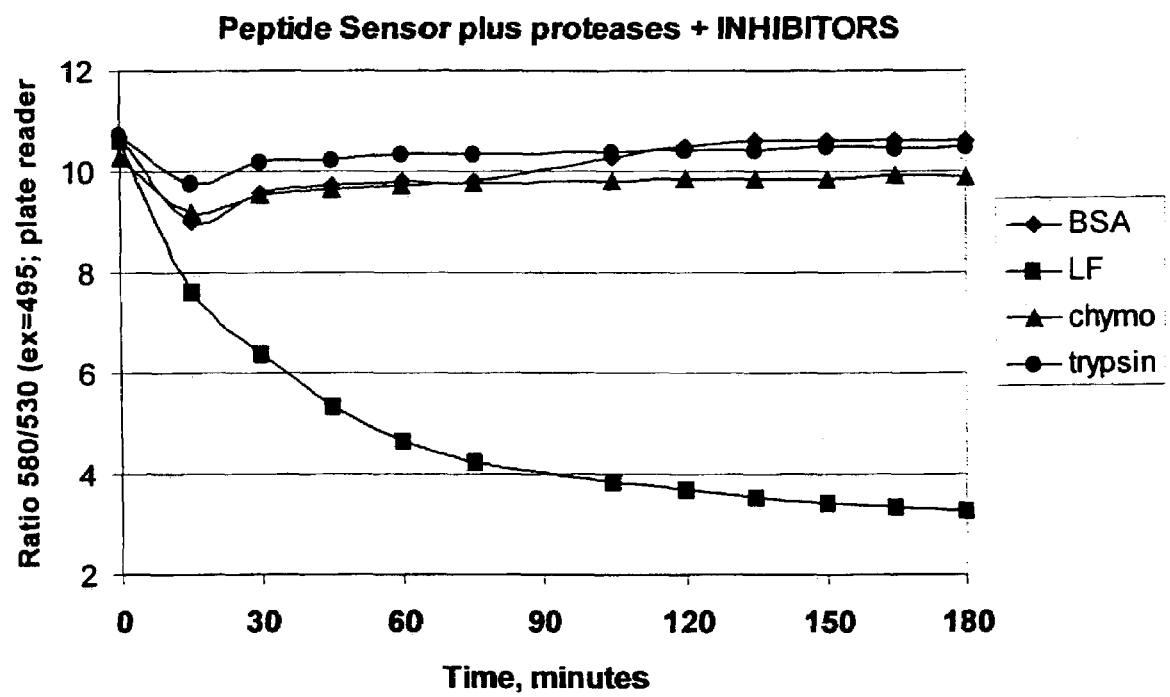
FIG. 4B. In the presence of the inhibitors the peptide was specifically cleaved by anthrax LF; no cleavage of the peptide by trypsin or chymotrypsin was disclosed.

Conditions for cleavage of peptide by LF. In addition to performing the cleavage reaction in PBS (pH 6.75), a parallel set of reactions was set up in which the sample buffer contained protease inhibitors (Calbiochem Protease Inhibitor cocktail #3, 1:100 dilution of the following stock: AEBSF (4-(2-aminoethyl)benzenesulfonylfluoride) at 100 mM; aprotinin at 80 μM; bestatin at 5 mM; E-64 at 1.5 mM; leupeptin at 2 mM; pepstatin A at 1 mM). In the presence of the inhibitors the peptide was cleaved by anthrax LF; no cleavage of the peptide by trypsin or chymotrypsin occurred (FIG. 4B). The rate of cleavage of the peptide by anthrax LF was unaffected by the inhibitors. Thus, the peptide is a detector of anthrax LF. Nonspecific zinc metalloproteases, such as thermolysin, would also not be inhibited in the reaction and could cleave the peptide.

Engineering of the Sensor. Modifications to the sensor peptide sequence to increase its sensitivity and specificity are made by removing recognition sites for undesirable protease activity. For example, the sequence is modified to remove the thermolysin cleavage site while retaining the LF site. Thermolysin is a bacterial protease from *Bacillus thermoproteolyticus* rokko, and not a known human toxin. Non-limiting examples of such variations to the sensor structure and their expected effects are listed in the table below.

| SEQ ID | Structure | Type | Description |
| --- | --- | --- | --- |
| 2 | MPKKKPTPIQLNP | peptide | native sequence of first 13 AA of MEK 1 protein |
| 3 | MPKKKPTPIQLNPC | peptide | peptide sequence used for biosensor |
| 4 | MPKKKPTPIYLNPC | peptide | engineered sequence for LF substrate |
| 5 | MPKKKPHPIQLNPC | peptide | engineered sequence for LF substrate |
| 6 | MPKKKPHPIYLNPC | peptide | engineered sequence for LF substrate |
| 7 | MPKKKPTPYQLNPC | peptide | engineered sequence for LF substrate, not a substrate for thermolysin |
| 8 | MPKKKPTPIPLNPC | peptide | engineered sequence for LF substrate, not a substrate for thermolysin |
| 9 | MPHHHPTPIQLNPC | peptide | engineered sequence for LF substrate, not a substrate for trypsin |
| 10 | MPHHHPTPTYLNPC | peptide | engineered sequence for LF substrate, not a substrate for trypsin |
| 11 | MPKKKPTPVQLNPC | peptide | engineered sequence for LF substrate |
| 12 | MPKKKPTPFQLNPC | peptide | engineered sequence for LF substrate |
| 13 | MPKKKPRPIQLNPC | peptide | engineered sequence for LF substrate |
| 14 | RRKPVLPALTI | peptide | MEK2 recognition site (cleavage at 2nd P) |
| 15 | SQQRNPGLIPK | peptide | MEK6 recognition site |

The use of a protease sensor for detecting anthrax protease is an improvement over current methods for detection of *Bacillus anthracis* employing PCR, which does not discriminate among live versus dead, or virulent vs. non-virulent strains of anthrax. Because the protease (lethal factor) is only expressed when the bacteria are viable and expressing the appropriate virulence factors, this sensor detects the most dangerous strains of this potential biological warfare agent. Therefore, a sensor of this type will have fewer false positives, which is desirable for a sensor to be used in a potentially hazardous situation.

I claim:

1. An isolated protease biosensor consisting of:
   a) a peptide consisting of the sequence of SEQ ID NO: 1
   b) a fluorescent donor molecule attached to the peptide that is capable of participating in fluorescence resonance energy transfer; and
   c) an acceptor molecule attached to the peptide that has an absorption spectrum overlapping the emission spectrum of the donor molecule, wherein the fluorescence donor molecule and the acceptor molecule are attached to amino acid residues that are on opposite sides of a protease cleavage site in the peptide.

2. An isolated protease biosensor consisting of:
   a) a peptide consisting of the sequence of SEQ ID NO: 2
   b) a fluorescent donor molecule attached to the peptide that is capable of participating in fluorescence resonance energy transfer; and
   c) an acceptor molecule attached to the peptide that has an absorption spectrum overlapping the emission spectrum of the donor molecule, wherein the fluorescence donor molecule and the acceptor molecule are attached to amino acid residues that are on opposite sides of a protease cleavage site in the peptide.

3. An isolated protease biosensor consisting of:
   a) a peptide consisting of an amino acid sequence of the general formula II:

R1-R2-R3-R4-R5-Pro-R6-R7-R-8-R9 wherein R1 is Lys; R2 is Lys; R3 is Lys; R4 is Pro; R5 is Thr; R6 is Ile; R7 is Gln; R8 is Leu; and R9 is Asn;
   b) a fluorescent donor molecule attached to the peptide that is capable of participating in fluorescence resonance energy transfer; and
   c) an acceptor molecule attached to the peptide that has an absorption spectrum overlapping the emission spectrum of the donor molecule, wherein the fluorescence donor molecule and the acceptor molecule are attached to amino acid residues that are on opposite sides of a protease cleavage site in the peptide.

* * * * *

SEQUENCE LISTING

<160> NUMBER OF SEQ ID NOS: 29

<210> SEQ ID NO 1
<211> LENGTH: 10
<212> TYPE: PRT
<213> ORGANISM: Artificial Sequence
<220> FEATURE:
<221> NAME/KEY: misc_feature
<223> OTHER INFORMATION: Synthetic peptide sequence

<400> SEQUENCE: 1

Lys Lys Lys Pro Thr Pro Ile Gln Leu Asn
1               5                   10

<210> SEQ ID NO 2
<211> LENGTH: 13
<212> TYPE: PRT
<213> ORGANISM: Artificial Sequence
<220> FEATURE:
<221> NAME/KEY: misc_feature
<223> OTHER INFORMATION: Synthetic peptide sequence

<400> SEQUENCE: 2

Met Pro Lys Lys Lys Pro Thr Pro Ile Gln Leu Asn Pro
1               5                   10

<210> SEQ ID NO 3
<211> LENGTH: 14
<212> TYPE: PRT
<213> ORGANISM: Artificial Sequence
<220> FEATURE:
<221> NAME/KEY: misc_feature
<223> OTHER INFORMATION: Synthetic peptide sequence

<400> SEQUENCE: 3

Met Pro Lys Lys Lys Pro Thr Pro Ile Gln Leu Asn Pro Cys
1               5                   10

<210> SEQ ID NO 4
<211> LENGTH: 14
<212> TYPE: PRT
<213> ORGANISM: Artificial Sequence
<220> FEATURE:
<221> NAME/KEY: misc_feature
<223> OTHER INFORMATION: Synthetic peptide sequence

<400> SEQUENCE: 4

Met Pro Lys Lys Lys Pro Thr Pro Ile Tyr Leu Asn Pro Cys
1               5                   10

<210> SEQ ID NO 5
<211> LENGTH: 14
<212> TYPE: PRT
<213> ORGANISM: Artificial Sequence
<220> FEATURE:
<221> NAME/KEY: misc_feature
<223> OTHER INFORMATION: Synthetic peptide sequence

<400> SEQUENCE: 5

Met Pro Lys Lys Lys Pro His Pro Ile Gln Leu Asn Pro Cys
1               5                   10

<210> SEQ ID NO 6
<211> LENGTH: 14
<212> TYPE: PRT
<213> ORGANISM: Artificial Sequence

```
<220> FEATURE:
<221> NAME/KEY: misc_feature
<223> OTHER INFORMATION: Synthetic peptide sequence

<400> SEQUENCE: 6

Met Pro Lys Lys Lys Pro His Pro Ile Tyr Leu Asn Pro Cys
1               5                   10

<210> SEQ ID NO 7
<211> LENGTH: 14
<212> TYPE: PRT
<213> ORGANISM: Artificial Sequence
<220> FEATURE:
<221> NAME/KEY: misc_feature
<223> OTHER INFORMATION: Synthetic peptide sequence

<400> SEQUENCE: 7

Met Pro Ser Ser Ser Pro Thr Pro Ile Gln Leu Asn Pro Cys
1               5                   10

<210> SEQ ID NO 8
<211> LENGTH: 14
<212> TYPE: PRT
<213> ORGANISM: Artificial Sequence
<220> FEATURE:
<221> NAME/KEY: misc_feature
<223> OTHER INFORMATION: Synthetic peptide sequence

<400> SEQUENCE: 8

Met Pro Ser Ser Ser Pro Thr Pro Ile Tyr Leu Asn Pro Cys
1               5                   10

<210> SEQ ID NO 9
<211> LENGTH: 14
<212> TYPE: PRT
<213> ORGANISM: Artificial Sequence
<220> FEATURE:
<221> NAME/KEY: misc_feature
<223> OTHER INFORMATION: Synthetic peptide sequence

<400> SEQUENCE: 9

Met Pro Lys Lys Lys Pro Thr Pro Tyr Gln Leu Asn Pro Cys
1               5                   10

<210> SEQ ID NO 10
<211> LENGTH: 14
<212> TYPE: PRT
<213> ORGANISM: Artificial Sequence
<220> FEATURE:
<221> NAME/KEY: misc_feature
<223> OTHER INFORMATION: Synthetic peptide sequence

<400> SEQUENCE: 10

Met Pro Lys Lys Lys Pro Thr Pro Ile Pro Leu Asn Pro Cys
1               5                   10

<210> SEQ ID NO 11
<211> LENGTH: 14
<212> TYPE: PRT
<213> ORGANISM: Artificial Sequence
<220> FEATURE:
<221> NAME/KEY: misc_feature
<223> OTHER INFORMATION: Synthetic peptide sequence

<400> SEQUENCE: 11

Met Pro Lys Lys Lys Pro Thr Pro Val Gln Leu Asn Pro Cys
1               5                   10
```

```
<210> SEQ ID NO 12
<211> LENGTH: 14
<212> TYPE: PRT
<213> ORGANISM: Artificial Sequence
<220> FEATURE:
<221> NAME/KEY: misc_feature
<223> OTHER INFORMATION: Synthetic peptide sequence

<400> SEQUENCE: 12

Met Pro Lys Lys Lys Pro Thr Pro Phe Gln Leu Asn Pro Cys
1               5                   10

<210> SEQ ID NO 13
<211> LENGTH: 14
<212> TYPE: PRT
<213> ORGANISM: Artificial Sequence
<220> FEATURE:
<221> NAME/KEY: misc_feature
<223> OTHER INFORMATION: Synthetic peptide sequence

<400> SEQUENCE: 13

Met Pro Lys Lys Lys Pro Arg Pro Ile Gln Leu Asn Pro Cys
1               5                   10

<210> SEQ ID NO 14
<211> LENGTH: 11
<212> TYPE: PRT
<213> ORGANISM: Artificial Sequence
<220> FEATURE:
<221> NAME/KEY: misc_feature
<223> OTHER INFORMATION: Synthetic peptide sequence

<400> SEQUENCE: 14

Arg Arg Lys Pro Val Leu Pro Ala Leu Thr Ile
1               5                   10

<210> SEQ ID NO 15
<211> LENGTH: 11
<212> TYPE: PRT
<213> ORGANISM: Artificial Sequence
<220> FEATURE:
<221> NAME/KEY: misc_feature
<223> OTHER INFORMATION: Synthetic peptide sequence

<400> SEQUENCE: 15

Ser Gln Gln Arg Asn Pro Gly Leu Ile Pro Lys
1               5                   10

<210> SEQ ID NO 16
<211> LENGTH: 39
<212> TYPE: DNA
<213> ORGANISM: Artificial Sequence
<220> FEATURE:
<221> NAME/KEY: misc_feature
<223> OTHER INFORMATION: Synthetic nucleotide sequence
<220> FEATURE:
<221> NAME/KEY: misc_feature
<222> LOCATION: (6)..(6)
<223> OTHER INFORMATION: n stands for a, t, c, or g.
<220> FEATURE:
<221> NAME/KEY: misc_feature
<222> LOCATION: (18)..(18)
<223> OTHER INFORMATION: n stands for a, t, c, or g.
<220> FEATURE:
<221> NAME/KEY: misc_feature
<222> LOCATION: (21)..(21)
<223> OTHER INFORMATION: n stands for a, t, c, or g.
<220> FEATURE:
<221> NAME/KEY: misc_feature
<222> LOCATION: (24)..(24)
```

```
<223> OTHER INFORMATION: n stands for a, t, c, or g.
<220> FEATURE:
<221> NAME/KEY: misc_feature
<222> LOCATION: (33)..(33)
<223> OTHER INFORMATION: n stands for a, t, c, or g.
<220> FEATURE:
<221> NAME/KEY: misc_feature
<222> LOCATION: (39)..(39)
<223> OTHER INFORMATION: n stands for a, t, c, or g.

<400> SEQUENCE: 16
atgccnaara araarccnac nccnathcar ytnaayccn                                  39

<210> SEQ ID NO 17
<211> LENGTH: 42
<212> TYPE: DNA
<213> ORGANISM: Artificial Sequence
<220> FEATURE:
<221> NAME/KEY: misc_feature
<223> OTHER INFORMATION: Synthetic nucleotide sequence
<220> FEATURE:
<221> NAME/KEY: misc_feature
<222> LOCATION: (6)..(6)
<223> OTHER INFORMATION: n stands for a, t, c, or g.
<220> FEATURE:
<221> NAME/KEY: misc_feature
<222> LOCATION: (18)..(18)
<223> OTHER INFORMATION: n stands for a, t, c, or g.
<220> FEATURE:
<221> NAME/KEY: misc_feature
<222> LOCATION: (21)..(21)
<223> OTHER INFORMATION: n stands for a, t, c, or g.
<220> FEATURE:
<221> NAME/KEY: misc_feature
<222> LOCATION: (24)..(24)
<223> OTHER INFORMATION: n stands for a, t, c, or g.
<220> FEATURE:
<221> NAME/KEY: misc_feature
<222> LOCATION: (33)..(33)
<223> OTHER INFORMATION: n stands for a, t, c, or g.
<220> FEATURE:
<221> NAME/KEY: misc_feature
<222> LOCATION: (39)..(39)
<223> OTHER INFORMATION: n stands for a, t, c, or g.

<400> SEQUENCE: 17
atgccnaara araarccnac nccnathcar ytnaayccnt gy                              42

<210> SEQ ID NO 18
<211> LENGTH: 42
<212> TYPE: DNA
<213> ORGANISM: Artificial Sequence
<220> FEATURE:
<221> NAME/KEY: misc_feature
<223> OTHER INFORMATION: Synthetic nucleotide sequence
<220> FEATURE:
<221> NAME/KEY: misc_feature
<222> LOCATION: (6)..(6)
<223> OTHER INFORMATION: n stands for a, t, c, or g.
<220> FEATURE:
<221> NAME/KEY: misc_feature
<222> LOCATION: (18)..(18)
<223> OTHER INFORMATION: n stands for a, t, c, or g.
<220> FEATURE:
<221> NAME/KEY: misc_feature
<222> LOCATION: (21)..(21)
<223> OTHER INFORMATION: n stands for a, t, c, or g.
<220> FEATURE:
<221> NAME/KEY: misc_feature
<222> LOCATION: (24)..(24)
<223> OTHER INFORMATION: n stands for a, t, c, or g.
<220> FEATURE:
<221> NAME/KEY: misc_feature
<222> LOCATION: (33)..(33)
<223> OTHER INFORMATION: n stands for a, t, c, or g.
```

```
<220> FEATURE:
<221> NAME/KEY: misc_feature
<222> LOCATION: (39)..(39)
<223> OTHER INFORMATION: n stands for a, t, c, or g.

<400> SEQUENCE: 18
atgccnaara araarccnac nccnathtay ytnaayccnt gy                           42

<210> SEQ ID NO 19
<211> LENGTH: 42
<212> TYPE: DNA
<213> ORGANISM: Artificial Sequence
<220> FEATURE:
<221> NAME/KEY: misc_feature
<223> OTHER INFORMATION: Synthetic nucleotide sequence
<220> FEATURE:
<221> NAME/KEY: misc_feature
<222> LOCATION: (6)..(6)
<223> OTHER INFORMATION: n stands for a, t, c, or g.
<220> FEATURE:
<221> NAME/KEY: misc_feature
<222> LOCATION: (18)..(18)
<223> OTHER INFORMATION: n stands for a, t, c, or g.
<220> FEATURE:
<221> NAME/KEY: misc_feature
<222> LOCATION: (24)..(24)
<223> OTHER INFORMATION: n stands for a, t, c, or g.
<220> FEATURE:
<221> NAME/KEY: misc_feature
<222> LOCATION: (33)..(33)
<223> OTHER INFORMATION: n stands for a, t, c, or g.
<220> FEATURE:
<221> NAME/KEY: misc_feature
<222> LOCATION: (39)..(39)
<223> OTHER INFORMATION: n stands for a, t, c, or g.

<400> SEQUENCE: 19
atgccnaara araarccnca yccnathcar ytnaayccnt gy                           42

<210> SEQ ID NO 20
<211> LENGTH: 42
<212> TYPE: DNA
<213> ORGANISM: Artificial Sequence
<220> FEATURE:
<221> NAME/KEY: misc_feature
<223> OTHER INFORMATION: Synthetic nucleotide sequence
<220> FEATURE:
<221> NAME/KEY: misc_feature
<222> LOCATION: (6)..(6)
<223> OTHER INFORMATION: n stands for a, t, c, or g.
<220> FEATURE:
<221> NAME/KEY: misc_feature
<222> LOCATION: (18)..(18)
<223> OTHER INFORMATION: n stands for a, t, c, or g.
<220> FEATURE:
<221> NAME/KEY: misc_feature
<222> LOCATION: (24)..(24)
<223> OTHER INFORMATION: n stands for a, t, c, or g.
<220> FEATURE:
<221> NAME/KEY: misc_feature
<222> LOCATION: (33)..(33)
<223> OTHER INFORMATION: n stands for a, t, c, or g.
<220> FEATURE:
<221> NAME/KEY: misc_feature
<222> LOCATION: (39)..(39)
<223> OTHER INFORMATION: n stands for a, t, c, or g.

<400> SEQUENCE: 20
atgccnaara araarccnca yccnathtay ytnaayccnt gy                           42

<210> SEQ ID NO 21
<211> LENGTH: 42
<212> TYPE: DNA
```

```
<213> ORGANISM: Artificial Sequence
<220> FEATURE:
<221> NAME/KEY: misc_feature
<223> OTHER INFORMATION: Synthetic nucleotide sequence
<220> FEATURE:
<221> NAME/KEY: misc_feature
<222> LOCATION: (6)..(6)
<223> OTHER INFORMATION: n stands for a, t, c, or g.
<220> FEATURE:
<221> NAME/KEY: misc_feature
<222> LOCATION: (18)..(18)
<223> OTHER INFORMATION: n stands for a, t, c, or g.
<220> FEATURE:
<221> NAME/KEY: misc_feature
<222> LOCATION: (21)..(21)
<223> OTHER INFORMATION: n stands for a, t, c, or g.
<220> FEATURE:
<221> NAME/KEY: misc_feature
<222> LOCATION: (24)..(24)
<223> OTHER INFORMATION: n stands for a, t, c, or g.
<220> FEATURE:
<221> NAME/KEY: misc_feature
<222> LOCATION: (33)..(33)
<223> OTHER INFORMATION: n stands for a, t, c, or g.
<220> FEATURE:
<221> NAME/KEY: misc_feature
<222> LOCATION: (39)..(39)
<223> OTHER INFORMATION: n stands for a, t, c, or g.

<400> SEQUENCE: 21
atgccnaara araarccnac nccntaycar ytnaayccnt gy                              42

<210> SEQ ID NO 22
<211> LENGTH: 42
<212> TYPE: DNA
<213> ORGANISM: Artificial Sequence
<220> FEATURE:
<221> NAME/KEY: misc_feature
<223> OTHER INFORMATION: Synthetic nucleotide sequence
<220> FEATURE:
<221> NAME/KEY: misc_feature
<222> LOCATION: (6)..(6)
<223> OTHER INFORMATION: n stands for a, t, c, or g.
<220> FEATURE:
<221> NAME/KEY: misc_feature
<222> LOCATION: (18)..(18)
<223> OTHER INFORMATION: n stands for a, t, c, or g.
<220> FEATURE:
<221> NAME/KEY: misc_feature
<222> LOCATION: (21)..(21)
<223> OTHER INFORMATION: n stands for a, t, c, or g.
<220> FEATURE:
<221> NAME/KEY: misc_feature
<222> LOCATION: (24)..(24)
<223> OTHER INFORMATION: n stands for a, t, c, or g.
<220> FEATURE:
<221> NAME/KEY: misc_feature
<222> LOCATION: (30)..(30)
<223> OTHER INFORMATION: n stands for a, t, c, or g.
<220> FEATURE:
<221> NAME/KEY: misc_feature
<222> LOCATION: (33)..(33)
<223> OTHER INFORMATION: n stands for a, t, c, or g.
<220> FEATURE:
<221> NAME/KEY: misc_feature
<222> LOCATION: (39)..(39)
<223> OTHER INFORMATION: n stands for a, t, c, or g.

<400> SEQUENCE: 22
atgccnaara araarccnac nccnathccn ytnaayccnt gy                              42

<210> SEQ ID NO 23
<211> LENGTH: 42
<212> TYPE: DNA
<213> ORGANISM: Artificial Sequence
```

```
<220> FEATURE:
<221> NAME/KEY: misc_feature
<223> OTHER INFORMATION: Synthetic nucleotide sequence
<220> FEATURE:
<221> NAME/KEY: misc_feature
<222> LOCATION: (6)..(6)
<223> OTHER INFORMATION: n stands for a, t, c, or g.
<220> FEATURE:
<221> NAME/KEY: misc_feature
<222> LOCATION: (18)..(18)
<223> OTHER INFORMATION: n stands for a, t, c, or g.
<220> FEATURE:
<221> NAME/KEY: misc_feature
<222> LOCATION: (21)..(21)
<223> OTHER INFORMATION: n stands for a, t, c, or g.
<220> FEATURE:
<221> NAME/KEY: misc_feature
<222> LOCATION: (24)..(24)
<223> OTHER INFORMATION: n stands for a, t, c, or g.
<220> FEATURE:
<221> NAME/KEY: misc_feature
<222> LOCATION: (33)..(33)
<223> OTHER INFORMATION: n stands for a, t, c, or g.
<220> FEATURE:
<221> NAME/KEY: misc_feature
<222> LOCATION: (39)..(39)
<223> OTHER INFORMATION: n stands for a, t, c, or g.

<400> SEQUENCE: 23
atgccncayc aycayccnac nccnathcar ytnaayccnt gy                           42

<210> SEQ ID NO 24
<211> LENGTH: 42
<212> TYPE: DNA
<213> ORGANISM: Artificial Sequence
<220> FEATURE:
<221> NAME/KEY: misc_feature
<223> OTHER INFORMATION: Synthetic nucleotide sequence
<220> FEATURE:
<221> NAME/KEY: misc_feature
<222> LOCATION: (6)..(6)
<223> OTHER INFORMATION: n stands for a, t, c, or g.
<220> FEATURE:
<221> NAME/KEY: misc_feature
<222> LOCATION: (18)..(18)
<223> OTHER INFORMATION: n stands for a, t, c, or g.
<220> FEATURE:
<221> NAME/KEY: misc_feature
<222> LOCATION: (21)..(21)
<223> OTHER INFORMATION: n stands for a, t, c, or g.
<220> FEATURE:
<221> NAME/KEY: misc_feature
<222> LOCATION: (24)..(24)
<223> OTHER INFORMATION: n stands for a, t, c, or g.
<220> FEATURE:
<221> NAME/KEY: misc_feature
<222> LOCATION: (33)..(33)
<223> OTHER INFORMATION: n stands for a, t, c, or g.
<220> FEATURE:
<221> NAME/KEY: misc_feature
<222> LOCATION: (39)..(39)
<223> OTHER INFORMATION: n stands for a, t, c, or g.

<400> SEQUENCE: 24
atgccncayc aycayccnac nccnathtay ytnaayccnt gy                           42

<210> SEQ ID NO 25
<211> LENGTH: 42
<212> TYPE: DNA
<213> ORGANISM: Artificial Sequence
<220> FEATURE:
<221> NAME/KEY: misc_feature
<223> OTHER INFORMATION: Synthetic nucleotide sequence
<220> FEATURE:
<221> NAME/KEY: misc_feature
```

```
<222> LOCATION: (6)..(6)
<223> OTHER INFORMATION: n stands for a, t, c, or g.
<220> FEATURE:
<221> NAME/KEY: misc_feature
<222> LOCATION: (18)..(18)
<223> OTHER INFORMATION: n stands for a, t, c, or g.
<220> FEATURE:
<221> NAME/KEY: misc_feature
<222> LOCATION: (21)..(21)
<223> OTHER INFORMATION: n stands for a, t, c, or g.
<220> FEATURE:
<221> NAME/KEY: misc_feature
<222> LOCATION: (24)..(24)
<223> OTHER INFORMATION: n stands for a, t, c, or g.
<220> FEATURE:
<221> NAME/KEY: misc_feature
<222> LOCATION: (27)..(27)
<223> OTHER INFORMATION: n stands for a, t, c, or g.
<220> FEATURE:
<221> NAME/KEY: misc_feature
<222> LOCATION: (33)..(33)
<223> OTHER INFORMATION: n stands for a, t, c, or g.
<220> FEATURE:
<221> NAME/KEY: misc_feature
<222> LOCATION: (39)..(39)
<223> OTHER INFORMATION: n stands for a, t, c, or g.

<400> SEQUENCE: 25
atgccnaara araarccnac nccngtncar ytnaayccnt gy                          42

<210> SEQ ID NO 26
<211> LENGTH: 42
<212> TYPE: DNA
<213> ORGANISM: Artificial Sequence
<220> FEATURE:
<221> NAME/KEY: misc_feature
<223> OTHER INFORMATION: Synthetic nucleotide sequence
<220> FEATURE:
<221> NAME/KEY: misc_feature
<222> LOCATION: (6)..(6)
<223> OTHER INFORMATION: n stands for a, t, c, or g.
<220> FEATURE:
<221> NAME/KEY: misc_feature
<222> LOCATION: (18)..(18)
<223> OTHER INFORMATION: n stands for a, t, c, or g.
<220> FEATURE:
<221> NAME/KEY: misc_feature
<222> LOCATION: (21)..(21)
<223> OTHER INFORMATION: n stands for a, t, c, or g.
<220> FEATURE:
<221> NAME/KEY: misc_feature
<222> LOCATION: (24)..(24)
<223> OTHER INFORMATION: n stands for a, t, c, or g.
<220> FEATURE:
<221> NAME/KEY: misc_feature
<222> LOCATION: (33)..(33)
<223> OTHER INFORMATION: n stands for a, t, c, or g.
<220> FEATURE:
<221> NAME/KEY: misc_feature
<222> LOCATION: (39)..(39)
<223> OTHER INFORMATION: n stands for a, t, c, or g.

<400> SEQUENCE: 26
atgccnaara araarccnac nccnttycar ytnaayccnt gy                          42

<210> SEQ ID NO 27
<211> LENGTH: 42
<212> TYPE: DNA
<213> ORGANISM: Artificial Sequence
<220> FEATURE:
<221> NAME/KEY: misc_feature
<223> OTHER INFORMATION: Synthetic nucleotide sequence
<220> FEATURE:
<221> NAME/KEY: misc_feature
<222> LOCATION: (6)..(6)
```

<223> OTHER INFORMATION: n stands for a, t, c, or g.
<220> FEATURE:
<221> NAME/KEY: misc_feature
<222> LOCATION: (18)..(18)
<223> OTHER INFORMATION: n stands for a, t, c, or g.
<220> FEATURE:
<221> NAME/KEY: misc_feature
<222> LOCATION: (21)..(21)
<223> OTHER INFORMATION: n stands for a, t, c, or g.
<220> FEATURE:
<221> NAME/KEY: misc_feature
<222> LOCATION: (24)..(24)
<223> OTHER INFORMATION: n stands for a, t, c, or g.
<220> FEATURE:
<221> NAME/KEY: misc_feature
<222> LOCATION: (33)..(33)
<223> OTHER INFORMATION: n stands for a, t, c, or g.
<220> FEATURE:
<221> NAME/KEY: misc_feature
<222> LOCATION: (39)..(39)
<223> OTHER INFORMATION: n stands for a, t, c, or g.

<400> SEQUENCE: 27
atgccnaara araarccnmg nccnathcar ytnaayccnt gy                          42

<210> SEQ ID NO 28
<211> LENGTH: 33
<212> TYPE: DNA
<213> ORGANISM: Artificial Sequence
<220> FEATURE:
<221> NAME/KEY: misc_feature
<223> OTHER INFORMATION: Synthetic nucleotide sequence
<220> FEATURE:
<221> NAME/KEY: misc_feature
<222> LOCATION: (3)..(3)
<223> OTHER INFORMATION: n stands for a, t, c, or g.
<220> FEATURE:
<221> NAME/KEY: misc_feature
<222> LOCATION: (6)..(6)
<223> OTHER INFORMATION: n stands for a, t, c, or g.
<220> FEATURE:
<221> NAME/KEY: misc_feature
<222> LOCATION: (12)..(12)
<223> OTHER INFORMATION: n stands for a, t, c, or g.
<220> FEATURE:
<221> NAME/KEY: misc_feature
<222> LOCATION: (15)..(15)
<223> OTHER INFORMATION: n stands for a, t, c, or g.
<220> FEATURE:
<221> NAME/KEY: misc_feature
<222> LOCATION: (18)..(18)
<223> OTHER INFORMATION: n stands for a, t, c, or g.
<220> FEATURE:
<221> NAME/KEY: misc_feature
<222> LOCATION: (21)..(21)
<223> OTHER INFORMATION: n stands for a, t, c, or g.
<220> FEATURE:
<221> NAME/KEY: misc_feature
<222> LOCATION: (24)..(24)
<223> OTHER INFORMATION: n stands for a, t, c, or g.
<220> FEATURE:
<221> NAME/KEY: misc_feature
<222> LOCATION: (27)..(27)
<223> OTHER INFORMATION: n stands for a, t, c, or g.
<220> FEATURE:
<221> NAME/KEY: misc_feature
<222> LOCATION: (30)..(30)
<223> OTHER INFORMATION: n stands for a, t, c, or g.

<400> SEQUENCE: 28
mgnmgnaarc cngtnytncc ngcnytnacn ath                                    33

<210> SEQ ID NO 29
<211> LENGTH: 33
<212> TYPE: DNA

-continued

```
<213> ORGANISM: Artificial Sequence
<220> FEATURE:
<221> NAME/KEY: misc_feature
<223> OTHER INFORMATION: Synthetic nucleotide sequence
<220> FEATURE:
<221> NAME/KEY: misc_feature
<222> LOCATION: (3)..(3)
<223> OTHER INFORMATION: n stands for a, t, c, or g.
<220> FEATURE:
<221> NAME/KEY: misc_feature
<222> LOCATION: (12)..(12)
<223> OTHER INFORMATION: n stands for a, t, c, or g.
<220> FEATURE:
<221> NAME/KEY: misc_feature
<222> LOCATION: (18)..(18)
<223> OTHER INFORMATION: n stands for a, t, c, or g.
<220> FEATURE:
<221> NAME/KEY: misc_feature
<222> LOCATION: (21)..(21)
<223> OTHER INFORMATION: n stands for a, t, c, or g.
<220> FEATURE:
<221> NAME/KEY: misc_feature
<222> LOCATION: (24)..(24)
<223> OTHER INFORMATION: n stands for a, t, c, or g.
<220> FEATURE:
<221> NAME/KEY: misc_feature
<222> LOCATION: (30)..(30)
<223> OTHER INFORMATION: n stands for a, t, c, or g.

<400> SEQUENCE: 29
wsncarcarm gnaayccngg nytnathccn aar                              33
```